United States Patent [19]

Pospisil et al.

[11] Patent Number: 4,927,532

[45] Date of Patent: May 22, 1990

[54] DEVICE FOR THE COMPENSATION OF THE BASELINE DRIFT OF A CHROMATOGRAPHIC SEPARATING COLUMN

[75] Inventors: Peter Pospisil, Überlingen; Bruno Kolb, Owingen, both of Fed. Rep. of Germany

[73] Assignee: The Perkin-Elmer Corporation, Norwalk, Conn.

[21] Appl. No.: 304,365

[22] Filed: Jan. 31, 1989

Related U.S. Application Data

[63] Continuation of Ser. No. 623,884, Jun. 25, 1984, abandoned.

[30] Foreign Application Priority Data

Jul. 1, 1983 [DE] Fed. Rep. of Germany ....... 3323744

[51] Int. Cl.$^5$ ............................................. B01D 15/08
[52] U.S. Cl. .................................. 210/198.2; 210/656; 55/386; 422/70; 73/23.1; 73/61.1 C
[58] Field of Search ...................... 210/635, 656, 198.2; 55/67, 386; 422/70; 436/161; 73/23.1, 61.1 C

[56] References Cited

U.S. PATENT DOCUMENTS

| 3,043,127 | 7/1962 | Deford | 55/67 |
|---|---|---|---|
| 3,146,616 | 9/1964 | Lord | 55/67 |
| 3,225,521 | 12/1965 | Burow | 55/67 |
| 3,590,628 | 7/1971 | Orr | 73/23.1 |
| 3,797,300 | 3/1974 | Sato | 73/23.1 |
| 3,826,905 | 7/1974 | Valkama | 436/161 |
| 3,997,298 | 12/1976 | McLafferty | 436/161 |
| 4,063,911 | 12/1977 | Kruppa | 55/67 |
| 4,170,893 | 10/1989 | Kleiss | 73/23.1 |
| 4,274,967 | 6/1981 | Snyder | 55/67 |
| 4,283,201 | 8/1981 | Deford | 436/161 |

FOREIGN PATENT DOCUMENTS 130574 9/1987 European Pat. Off. ......... 210/198.2

Primary Examiner—Ernest G. Therkorn
Attorney, Agent, or Firm—Thomas P. Murphy; Edwin T. Grimes

[57] ABSTRACT

The baseline drift occurring during a temperature or flow rate program in a chromatographic separating column is compensated for by signals from a function generator. The function generator supplies a computed baseline signal which is a representation of the baseline drift as an analytic function of the temperature, computed with specific separating column parameters. The parameters are determined in a prior test run and inputted into the function generator.

2 Claims, 4 Drawing Sheets

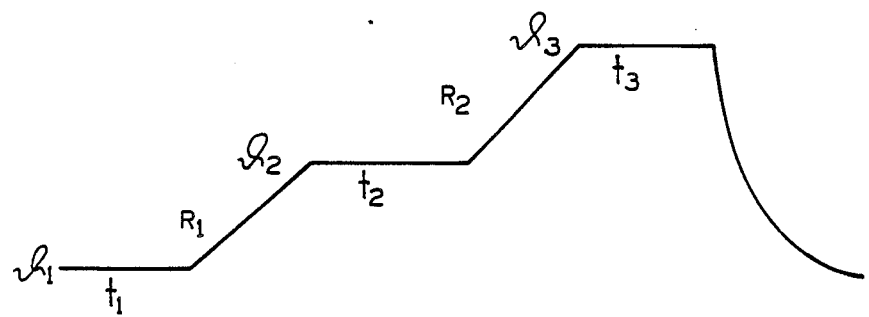
FIG. 2
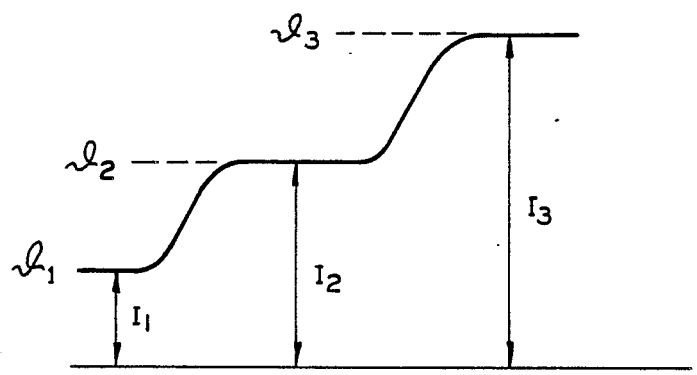
FIG. 3
$$X \rightarrow \boxed{\frac{1}{1 + r \cdot p}} \rightarrow Y$$
FIG. 4

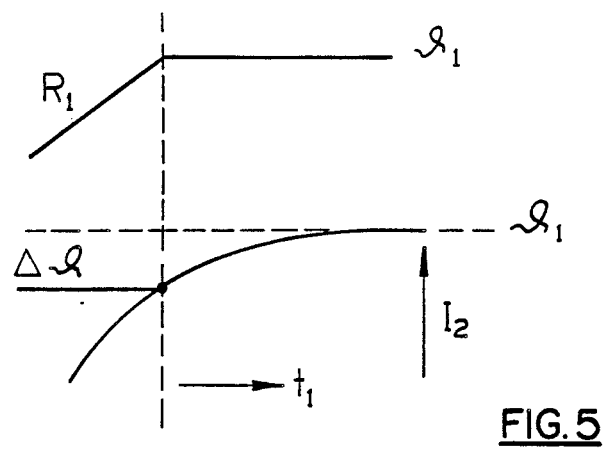
FIG. 5
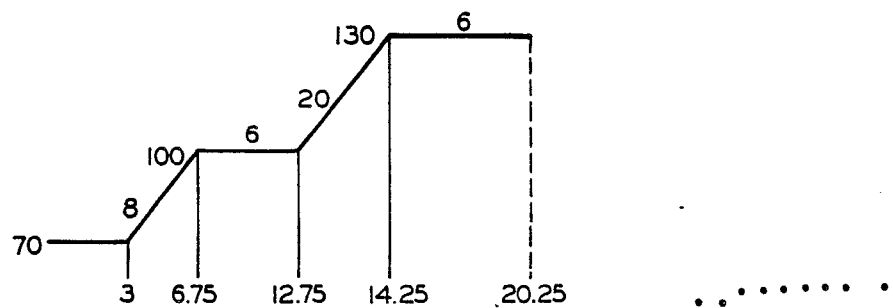
FIG. 6
FIG. 7
FIG. 8

DEVICE FOR THE COMPENSATION OF THE BASELINE DRIFT OF A CHROMATOGRAPHIC SEPARATING COLUMN

This is a continuation of application Ser. No. 06/623,884 filed on June 25, 1984, now abandoned.

BACKGROUND OF THE INVENTION

The present invention generally relates to a device for compensating the baseline drift of a chromatographic separating column during a temperature and/or flow program.

Mixtures are separated by chromatography (gas or liquid chromatography). A separating column contains a separating substance which interacts more or less intensely with the individual constituents of a mixture being examined. In many cases, the separating substance is a liquid in a stationary phase, in which the constituents of the mixture being examined are more or less soluble. A carrier medium (carrier gas or carrier liquid) is conducted through the separating column with a certain flow rate. The mixture to be examined is supplied to the inlet of the separating column and transported by the carrier medium through the separating column. Therein a constituent which, for example, is easily soluble in a liquid stationary phase propagates through the separating column more slowly than a constituent which is less soluble or more volatilized in this stationary phase. Therefore, a sample mixture supplied as a "plug" to the inlet of the separating column separates on its way through the separating column into the individual constituents thereof. The individual constituents propagate through the separating column at different speeds and elute consecutively at the outlet of the separating column. A detector, which responds to the emerging constituents of the sample and supplies corresponding signals, is provided at the outlet of the column. The temporal behavior of the detector signal, in the form of a chromatogram, shows a sequence of bands or peaks, each of which corresponds to a constituent of the mixture.

Certain constituents of a sample propagate only very slowly through the separating column in comparison with other constituents. Therefore, when working at a constant temperature and flow rate, which ensures a proper separation of the easily volatilized constituents, it takes a very long time until the not so easily volatilized constituents appear. As a result, the time of analysis is prolonged. Furthermore, when the time of analysis is prolonged, the bands or peaks are undesirably widened. Therefore, in order to avoid these disadvantages, it is known to vary the temperature and possibly the flow rate according to a predetermined program. When the temperature of the separating column is increased with time according to a certain program, the less easily volatilized constituents are more quickly driven out of the separating column after the easily volatilized constituents have exited. An increase of the flow rate as a function of time has a similar effect.

The detector also supplies a signal when no sample is supplied to the separating column. This signal is constant with constant temperature and constant flow rate. In recording of the chromatogram, this signal results in a straight, horizontal baseline, to which the peaks can be referenced. With a temperture or flow rate program, however, the "baseline signal" varies with the variation of the temperature of the flow rate. This baseline signal variation has to be taken into account when evaluating the chromatogram. For this purpose it is known to provide a second similar reference separating column in addition to the "active" separating column used for separating the mixture. The reference separating column is operated without a sample mixture, but otherwise under identical conditions as the active separating column. The detector signal obtained from the outlet of the active separating column is corrected by the detector signal from the outlet of the reference separating column. However, such an arrangement is expensive. Two separating columns identically formed have to be provided with detectors and placed in an oven correspondingly dimensioned. Furthermore, the exact corresponding formation of the separating columns and the exact corresponding, programmed conditions of operation are necessary for accurate baseline compensation. Failure to meet this requirement can lead to measuring and identification errors.

Furthermore, it is known to store the profile of the baseline during a test run without the sample, but with the predetermined temperature or flow rate program. During a subsequent measuring run, the stored value of the baseline is subtracted from the respective measuring signal. This approach requires a rather high capacity memory. Furthermore, each time the progrm is changed, the baseline has to be recorded anew and stored.

SUMMARY OF THE INVENTION

Accordingly, it is one object of the present invention to provide a device for compensating for the baseline drift of a chromatographic separating column during a temperature and/or flow rate program, which is simplier than prior art such devises.

Another object of the present invention is to provide a device for compensating for the baseline drift of a chromatographic separating column during a temperature and/or flow rate program, which avoids measuring errors common with conventional apparatus.

Yet another object of the present invention is to provide a device for compensating for the baseline drift of a chromatographic separating column during a temperature and/or flow rate program, which only requires a single separating column.

These objects are accomplished, at least in part, by providing new and improved apparatus, which includes a separating column; means for heating the separating column according to a temperature and/or flow program; and detector means positioned to detect the elute from said separating column and to output a measuring signal corresponding to the eluted sample constituents from said column. Further, the apparatus includes function generator means for outputting a computed baseline signal; means for inputting to said function generator the temperature and/or flow program as well as predetermined parameters corresponding to the particular apparatus. In addition, the apparatus includes means for correcting the measured signal with the calculated baseline signal. According to one aspect of the invention the parameters are determined in a test run and supplied as input to calculating means for determining said parameters, which are then inputted to the function generator means.

Other objects and advantages will become apparent to those skilled in the art from the following detailed description read in conjunction with the appended claims and the drawings affixed hereto.

BRIEF DESCRIPTION OF THE DRAWINGS

FIG. 2 is a graphic representation of a temperature program for the determination of the parameters of the baseline function;

FIG. 3 is the profile of the baseline, corresponding to the temperature program of FIG. 2;

FIG. 4 is a mathematical model of the separating column;

FIG. 5 is a portion of the temperature program with a linear slope and a subsequent time interval of constant temperature and the corresponding column temperature profile;

FIG. 6 is a temperature program used for a measurement;

FIG. 7 is the baseline profile corresponding to the temperature program shown in FIG. 6;

FIG. 8 is the profile of the baseline signals supplied from a function generator;

DETAILED DESCRIPTION OF THE INVENTION

Figure 1:
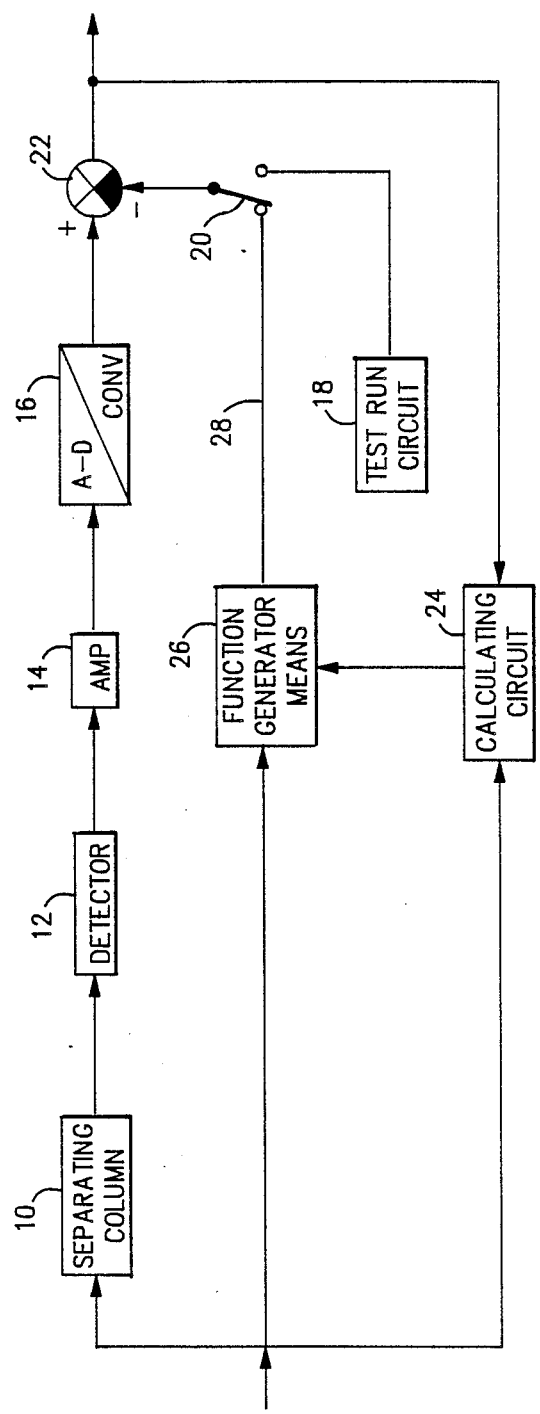
FIG. 1 is a block diagram of a device for the compensation of the baseline drift of a chromatographic separating column during a temperature program.

A separating column, generally indicated at 10 in FIG. 1, is adapted to be heated according to a temperature program. The temperature program is an input to the apparatus. The temperature program is characterized by three temperature levels $\theta_1$, $\theta_2$ and $\theta_3$, which exist, respectively, during the time intervals $t_1$, $t_2$ and $t_3$. The temperature program includes temperature increase rates, $R_1$ and $R_2$, during which the temperature increases between the temperature levels $\theta_1$ and $\theta_2$, and $\theta_2$ and $\theta_3$, respectively. A detector 12 is positioned to receive the elute at the outlet of the separating column 10. This detector is responsive to the emerging constituents of a mixture supplied as a sample. The sample is supplied to the inlet of the separating column 10 and transported by a carrier medium i.e. a solvent, through the column and is separated therein into its constituents. The signal from the detector 12 is amplified by an amplifier 14 and digitized by means of an A/D-converter 16. In the preferred embodiment, the signal processing is performed digitally by means of an appropriately programmed microprocessor. The signal processing can, however, also take place in an analog manner.

Initially, a test run is carried out during which no sample is supplied to the separating column 10. During this test run a test run circuit 18 is operative, which is symbolized in that the switch 20 is in its right indexing position in FIG. 1. During the test run the separating column 10 follows the temperature program as it is defined by the temperature levels, $\theta_1$, $\theta_2$ and $\Theta_3$, the time intervals, $t_1$, $t_2$ and $t_3$ and the temperature increase rates, $R_1$ and $R_2$, as illustrated in FIG. 2, while the test run circuit 18 provides, at the same time, the signal "zero" through switch 20 to a difference forming means 22. The means 22 also receives the output of the A/D-converter 16. Thus, the difference forming means 22 outputs an uncorrected detector signal which has the profile illustrated in FIG. 3. This detector signal is supplied to a calculating circuit 24, to which, in addition thereto, the temperature levels, $\theta_1$, $\theta_2$ and $\theta_3$, the time intervals, $t_1$, $t_2$ and $t_3$, and the increase rates, $R_1$ and $R_2$, are supplied. The calculating circuit 24 calculates therefrom the parameters of the function representing the baseline in a way to be described hereinbelow. These parameters are inputted into a function generator means 26.

The function generator means 26 are inoperative during the described test run, as it is indicated in FIG. 1 by the switch 20. During a subsequent measuring run, during which a sample is supplied to the separating column 10, the function generator means 26 receives as input the temperature program as it is defined by the temperature levels $\theta_1$, $\theta_2$ and $\theta_3$, the time intervals, $t_1$, $t_2$ and $t_3$, and increase rates, $R_1$ and $R_2$ (for example as shown in FIG. 6). The function generator 26 also receives as input the parameters from the calculating circuit 24. The function generator outputs as indicated at 28 a computed baseline signal. When the measuring signal as in the preferred embodiment is digitized, the function generator likewise supplies a signal in digital form. This signal from the function generator means 26 is substracted from the measuring signal by the difference forming means 22. The difference forming means 22 represents a means for correcting the measuring signal by subtracting the computed baseline signal.

The parameters of the computed baseline signal representing the actual baseline are calculated in the calculating circuit 24 in the following way.

The background current supplied, for example from a gas chromatography detector, depends on the bleeding of the separating column and thus on the type of the liquid stationary phase and its temperature function. This follows an exponential relationship:

$$I = a \cdot e^{b\theta} + I_o, \quad (1)$$

wherein:
I is the background current at a column temperature $\theta$,
$\theta$ is the column temperature,
$I_o$ is the background current from the detector, for example a flame ionization detector, and
a, b are column specific constants.

This basic equation contains three constants, whose values are unknown and which must therefore be determined experimentally. This is accomplished by operating the separating column at three different temperatures, as seen in the temperature program illustrated in FIG. 2.

Each isothermal time period during a test run corresponds to a certain background signal which can easily be determined. These background signals are $$I_1 = a \cdot e^{b \cdot \theta_1} + I_o \quad (2)$$

$$I_2 = a \cdot e^{b \cdot \theta_2} + I_o$$

$$I_3 = a \cdot e^{b \cdot \theta_3} + I_o$$

A set of three equations including three unknown values is thus obtained. Nevertheless, it is not possible to determine these three unknown constants by explicit calculation. The constants have to be determined by means of an iteration method. The constants b, a and $I_o$ are determined from the following equations:

$$b_{i+1} = \frac{1}{\theta_2 - \theta_1} \ln \left[ \frac{I_3 - I_2}{I_2 - I_1} \cdot \frac{e^{(\theta_2 - \theta_1) \cdot b_i} - 1}{e^{(\theta_2 - \theta_1) \cdot b_i} - 1} \right] \quad (3)$$

$$a = \frac{I_2 - I_1}{e^{\theta_1 \cdot b}} \cdot \frac{1}{e^{(\theta_2 - \theta_1) \cdot b} - 1} \qquad (4)$$

$$I_o = I_1 - a \cdot e^{b \cdot \theta_1} \qquad (5)$$

FIG. 3 shows the real profile of the baseline during a test run programmed according to the program of FIG. 2. The program parameters, such as the temperatures, are known from FIG. 2 and the corresponding currents can be derived from FIG. 3. As indicated above, the value of the constants a, b and $I_o$ can be determined from the baseline deflection during the corresponding isothermal time intervals. The real shape of the rounded baseline drift illustrated in FIG. 3 is caused by the time delay during the heat transfer from the oven to the separating column. Taking this effect into account, it becomes necessary to know the dynamic properties of the separating column. For this purpose, these are initially treated as a dynamic system with a first order time function element, as is illustrated in FIG. 4. If the input x of such a system is a linear function, for example, the liner program rise ($\theta = R \cdot t$), the output y is given by the following relationships:

$$\alpha[R \cdot t] = \frac{R}{p^2}$$

$$\alpha\left[\frac{R}{p^2(1 + \theta p)}\right] = F(p)$$

$$\alpha - 1[F(p)] = R \cdot \tau \left(e^{\frac{-t}{\tau}} + \frac{t}{\tau} - 1\right) = f(t)$$

wherein:
R is the rate of the program rise; and
$\zeta$ is the Laplace transformator.

From the function f(t) the actual column temperature, lagging behind the oven temperature, is given by $$\theta = \theta_1 + R_1 \cdot \left(e^{-\frac{t}{\tau}} + \frac{t}{\tau} - 1\right) \qquad (6)$$

The corresponding background current is $$I = a \cdot e^{b\theta_1 + R_1 \cdot (e^{-\frac{t}{\tau}} + \frac{t}{\tau} - 1)} + I_o \qquad (7)$$

The equations (6) and (7) hold for the first temperature increase starting from the first isothermal time interval at the temperature $\theta_1$. The subsequent temperature increase from the second isothermal time interval at the temperature $\theta_2$ with the rate $R_2$ of the program rise is described by $$I = a \cdot e^{b\theta_2 + R_2 \cdot (e^{-\frac{t}{\tau}} + \frac{t}{\tau} - 1)} + I_o \qquad (8)$$

The time constant $\tau$ must again be calculated according to an iterative method. This can be done according to the equation $$\tau_{i+1} = \frac{1}{R_1}(\theta_1 + R_1 \cdot t) + \tau_i e^{-\frac{t}{\tau_i}} \frac{1}{b \cdot R_1} \ln\left(\frac{I - I_o}{a}\right) \qquad (9)$$

or from the second temperature increase according to the equation $$\tau_{i+1} = \frac{1}{R_2}(\theta_2 + R_2 \cdot t) + \tau_i e^{-\frac{t}{\tau_i}} \frac{1}{b \cdot R_2} \ln\left(\frac{I - I_o}{a}\right) \qquad (10)$$

At the end of a heating procedure, when the temperature remains constant, the actual separating column temperature follows the oven temperature with a time delay. The background current obtained therein results in a continuous curve which approaches the final value more or less slowly depending on the time constant. It is $$\theta = \theta_1 - \Delta\theta \cdot e^{-\frac{t}{\tau}} \qquad (11)$$

which is graphically illustrated in FIG. 5.

Insertion of equation (11) results in a function which describes the true baseline behavior during the stabilization at a new temperature level:

$$I = a \cdot e^{b(\theta_1 - \Delta\theta \cdot e^{-\frac{t}{\tau}})} + I_o \qquad (12)$$

Figure 9:
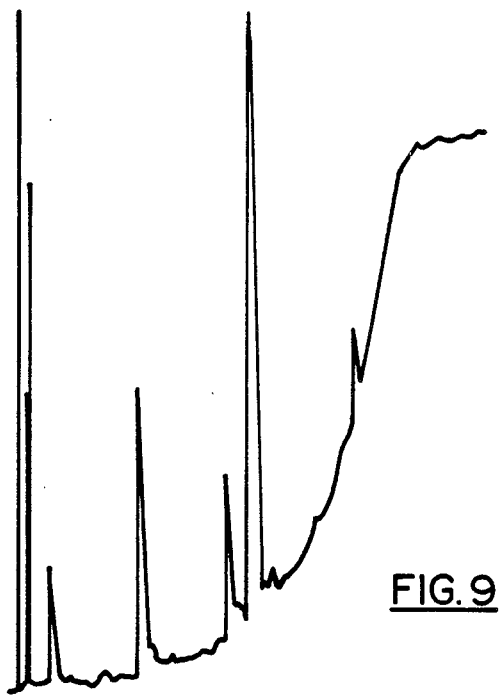
FIG. 9 is a chromatogram with a temperature program without compensation for the baseline drift.
Figure 10:
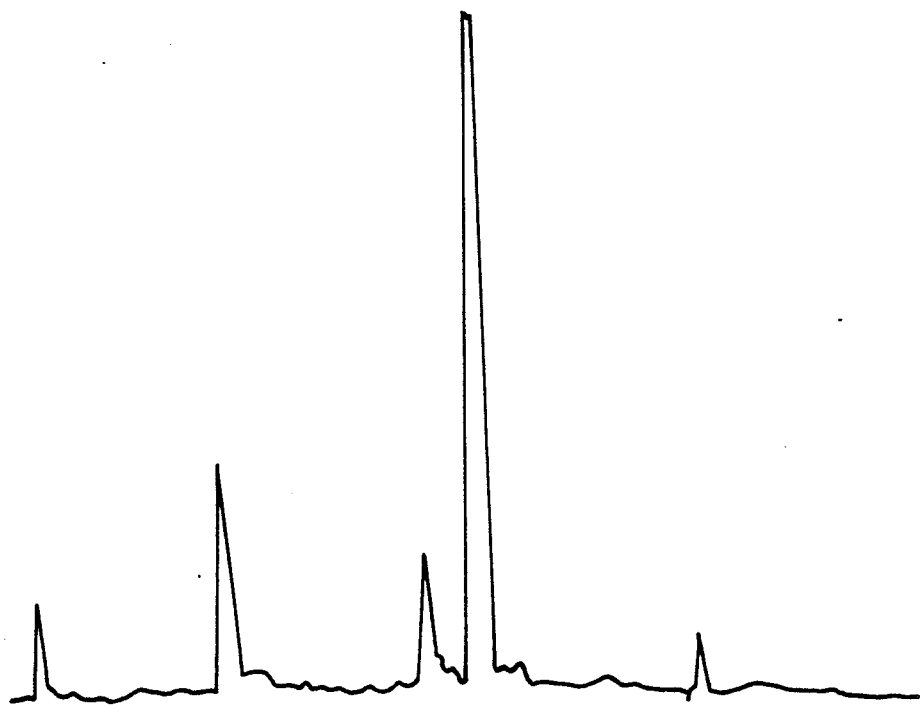
FIG. 10 is the chromatogram of FIG. 8 after compensation for the baseline drift.

The results, which are obtained with a device of the described type, are illustrated in FIGS. 6 to 10. FIGS. 6 to 8 show, for a "test run" without sample, the good coincidence between measured and calculated baseline. FIGS. 9 and 10 show the compensation of the baseline drift by means of a baseline signal calculated in the described way.

In the described example, the compensation for the baseline drift, caused by a temperature program, is described. The baseline drift caused by a flow rate program can be compensated for in an equivalent way.

We claim:
1. Device for the compensation of the baseline drift of a chromatographic separating column during a temperature and/or flow program, comprising,
   (a) a separating column,
   (b) programmer means, which are arranged to subject the separating column to predeterminable temperature and/or flowing programs,
   (c) test run means for providing a first temperature and/or flow program without sample feeding for determination of a baseline depending on the temperature and on the flow and characteristic for the separating column,
   (d) a memory arranged to memorize data of the baseline thus determined, and
   (e) difference forming means, to which, during the subsequent execution of a second temperature and/or flow program with sample feeding and with the same separating column,
   a measuring signal corresponding to the output of the separating column and
   a baseline signal obtained from the memorized data for correction of the measuring signal are adapted to be applied, comprising,

(i) computer means,
  to which the program parameters of the first temperature and/or flow program are applied by the test run means, and
  to which the uncorrected baseline signal obtained with this temperature and/or flow program without sample feeding is applied, and
  which are arranged to calculate parameters, a, b, $\tau$, Io, specific for the separating column of the analytic function of known form which represents the course of the baseline signal, and
(ii) function generator means,
  to which the parameters a, b, $\tau$, Io specific for the separating column and calculated by the computer means are adapted to be applied, and which are arranged to illustrate the baseline signal as said analytic function of time t of the program parameters $\theta_1$, $\theta_2$, $\theta_3$, $t_1$, $t_2$, $t_3$, $R_1$, $R_2$, of the temperature and/or flow program determined by the program supply means and of the parameters a, b, $\tau$, Io, specific for the separating column, and
(f) means for correcting said measuring signal with said computed baseline signal wherein:
a, b are columns specific constants;
$\tau$ is a time constant;
$\theta$, $\theta_2$, and $\theta_3$ are column temperatures;
$t_1$, $t_2$, and $t_3$ are times; and
$R_1$ and $R_2$ are increase rates.

2. A device according to claim 1 wherein said function generator means comprises calculating means for determining said column parameters corresponding to background current supplied according to the expotential relationship;

$$I = a \cdot e^{b(\theta_1 - \theta \cdot e^{-\frac{t}{\tau}})} + I_o$$

wherein:
I is the background current at a column temperature $\theta$;
$\theta$ is the column temperature;
$I_o$ is the background current from the detector;
a, b are columns specific constants;
t is the time;
$\tau$ is a time constant.

* * * * *